(12) United States Patent
Feng et al.

(10) Patent No.: US 9,840,627 B2
(45) Date of Patent: Dec. 12, 2017

(54) APPLICATION OF CAMPTOTHECIN AND DERIVATIVES THEREOF AS ANTIFOULING AGENT

(71) Applicant: Xiamen University, Xiamen, Fujian Province (CN)

(72) Inventors: Danqing Feng, Xiamen (CN); Caihuan Ke, Xiamen (CN); Wei Wang, Xiamen (CN); Xiang Wang, Xiamen (CN); Jian He, Xiamen (CN); Hui Liu, Xiamen (CN)

(73) Assignee: Xiamen University, Xiamen, Fujian Province (CN)

( * ) Notice: Subject to any disclaimer, the term of this patent is extended or adjusted under 35 U.S.C. 154(b) by 0 days.

(21) Appl. No.: 14/902,293

(22) PCT Filed: Oct. 16, 2013

(86) PCT No.: PCT/CN2013/085307
§ 371 (c)(1),
(2) Date: Dec. 30, 2015

(87) PCT Pub. No.: WO2015/000240
PCT Pub. Date: Jan. 8, 2015

(65) Prior Publication Data
US 2016/0264789 A1 Sep. 15, 2016

(30) Foreign Application Priority Data

Jul. 1, 2013 (CN) .......................... 2013 1 0270946

(51) Int. Cl.
*C09D 5/16* (2006.01)
*A01N 43/90* (2006.01)

(52) U.S. Cl.
CPC ........... *C09D 5/1625* (2013.01); *A01N 43/90* (2013.01); *C09D 5/16* (2013.01)

(58) Field of Classification Search
CPC ......... C09D 5/1625; C09D 5/16; A01N 43/90
See application file for complete search history.

(56) References Cited

U.S. PATENT DOCUMENTS

| 5,614,529 A | 3/1997 | Wall et al. |
| 2011/0256232 A1* | 10/2011 | Nygaard .............. A61K 35/612 424/520 |

FOREIGN PATENT DOCUMENTS

| CN | 1218820 A | 6/1999 |
| CN | 1802913 A | 7/2006 |
| CN | 102895229 A | 1/2013 |
| CN | 103289461 A | 9/2013 |
| WO | 96/09049 A1 | 3/1996 |
| WO | 2010049454 A2 | 5/2010 |
| WO | 2011071892 A2 | 6/2011 |

OTHER PUBLICATIONS

Li, S. et al. "Antifungal Activity of Camptothecin, Trifolin, and Hyperoside Isolated from Camptotheca acuminata" J. Agric. Food Chem. 2005, 53, 32-37.*
IPPIC (http://www.ippic.org/site/assets/docs/Public%20AFWG/IPPIC%20Function%20of%20Zinc%20Oxide%20in%20antifouling%20paints%20final%20draft%20March%201%202012.pdf) "Function of Zinc Oxide in Antifouling Paints" Mar. 1, 2012, p. 1-2.*
Zhang, Liqin et al., Antifungal activity of camptothecin on Rhizoctonia solani, Sphaerotheca fuliginea and Pseudoperonospora cubensis, Journal of Zhejiang Forestry College, 2008, 25(6): 681-684 (English Abstract).
Ying et al., Chemical Research and Application, Progress in Research of Structure Modification and Structure-Activity of Camptothecin and Its Analogues, Dec. 2003, pp. 744-748, vol. 15, No. 6. (English Abstract.).
English Translation of the PCT International Search Report dated Apr. 10, 2014 for International Application No. PCT/CN2013/085307 (2 pages).

* cited by examiner

*Primary Examiner* — Yong S Kwon
*Assistant Examiner* — Andrew S Rosenthal
(74) *Attorney, Agent, or Firm* — Fitch, Even, Tabin & Flannery, LLP (57) ABSTRACT

The present invention provides application of camptothecin and derivatives thereof as antifouling agent, relating to camptothecin. Application of camptothecin and derivatives thereof as antifouling agent for facilities in water is provided, wherein the antifouling agent contains camptothecin and/or at least one of its derivatives. The application of camptothecin and derivatives thereof as antifouling agent for facilities in water can be used to prevent attachment of marine or freshwater micro-fouling organisms and/or large fouling organisms to the surfaces of facilities in the sea, lake, river or pool. The antifouling agent may also be used in mixture with other antifouling substance. Antifouling method for artificial facilities in water is provided. An antifouling paint for facilities in water is provided. Camptothecin and its derivatives have significant inhibitory activity to the attachment of fouling organisms, i.e. having antifouling activity, and can be used to prevent the attachment of fouling organisms on the surfaces of artificial facilities in water. Camptothecin and its derivatives have high antifouling activity, good antifouling efficiency, and broad-spectrum antifouling.

6 Claims, 2 Drawing Sheets

APPLICATION OF CAMPTOTHECIN AND DERIVATIVES THEREOF AS ANTIFOULING AGENT

CROSS-REFERENCE TO RELATED APPLICATIONS

This application is a U.S. national phase application filed under 35 U.S.C. §371 of International Application PCT/CN2013/085307, filed Oct. 16, 2013, designating the United States, which claims priority from Chinese Application CN 201310270946.5, filed Jul. 1, 2013, which are all hereby incorporated herein by reference in their entirety.

FIELD OF THE INVENTION

The present invention relates to camptothecin, particularly application of camptothecin and derivatives thereof as antifouling agent.

DESCRIPTION OF THE PRIOR ART

In the history of using ocean and exploiting ocean resources, human has been always facing with the problem of controlling marine fouling organisms. The marine fouling organisms are the marine organisms attaching to or growing on the surfaces of vessels and marine artificial facilities in the marine environment, which adversely affect human economic activities. In the marine environment, when an object is immersed in seawater, micro-fouling first occurs on its surface, i.e. bacteria and other microorganisms attach to the surface of the object, and then grow and multiply on it; subsequently, bugulas, barnacles, mussels and other marine organisms attach to the surface of the object forming a marine fouling biocenoses. That the marine fouling organisms attach to the surfaces of vessels and marine artificial facilities can result in increased navigational resistance of vessel, reduced navigational speed, increased fuel consumption, clogged meshes of mariculture net bins, net cages, culture fencing nets, set fishing netting and the like, blocked seawater transportation pipelines, malfunction of instruments and rotating mechanisms in the sea, impact on the normal use of acoustic instruments, buoys, nets, valves and other facilities, increased burden on the platforms of oil and natural gas exploitation, accelerated metallic corrosion of the vessels and marine facilities, which severely endangers marine engineering, marine transportation, mariculture and naval equipment, and causes enormous economic loss.

So far, the most economical, effective and common method of solving marine biofouling is to brush the surface of the marine equipment with a paint containing marine antifouling agent, the main role of which is killing or repelling the marine fouling organisms through a gradual release of the paint's key component—marine antifouling agent to achieve the purpose of preventing the marine fouling organisms from attaching to the surface of marine artificial facilities. Organotin compounds were wildly used as marine antifouling agents, but they are highly toxic to the marine organisms and prone to accumulate in the bodies of the organisms with a slow degradation, which has a serious impact on the marine ecological environment. And the organotin compounds enter human bodies through food chain, causing adverse effects on human sex hormones and lymphocytes. They are considered as one of the most toxic hazardous substances which have been introduced to the marine environment by far. Hence, in 2001 the IMO (International Maritime Organization) passed a resolution on the deadline of the use of organotin compounds, which demanded that spraying paints containing organotin compounds on vessels should be worldwide banned since Jan. 1, 2003 and the organotin antifouling paints should no longer exist on any operating vessel since Jan. 1, 2008. At present, cuprous oxide is used as the primary marine antifouling agent, but extensive use of it could also seriously damage the marine ecological balance. Some European countries have already banned or restricted vessels brushed with cuprous oxide antifouling paints to enter the harbors. Therefore, with the enhancement of the awareness of environmental protection, the rapid development of marine economy, and the use of toxic heavy metal antifouling agents being successively banned or restricted, the development of new environmentally friendly marine antifouling agent becomes an urgent problem to be solved.

Camptothecin (CPT) is a quinoline alkaloid, which was extracted from Chinese unique Davidiaceae plant *Camptotheca acuminata* by American scientist Monroe E. Wall for the first time in 1966. *Camptotheca acuminata*'s fruit, velamen, root, bark, tender leaf, seed and other tissues all contain camptothecin. The chemical compound has significant anticancer activity, and has certain curative effect on various malignant tumors like stomach cancer, colon cancer, liver cancer, chronic granulocytic hemophilia, which draws an extensive attention. Through semi-synthesis, full synthesis and structural modification, a number of camptothecin derivatives have been prepared. The study has found that the anticancer mechanism of camptothecin and its derivatives is to inhibit DNA topoisomerase I (Topo I) to interfere with the DNA replication of the tumor cells and accordingly to inhibit the growth of the tumor cells. Furthermore, the Chinese invention patent with Publication Number CN102895229A has also disclosed the medical application of camptothecin and its derivatives in anti-Alzheimer's disease. Camptothecin compounds are also used in preparation of botanical bio-pesticides. American patent U.S. Pat. No. 5,614,529A has also disclosed that camptothecin compounds have inhibitory effect on the growth of plasmodia, and they can be used to treat the *plasmodium* infection of human and animal. So far, there are no reports about camptothecin and its derivatives used as antifouling agent.

SUMMARY OF THE INVENTION

The present invention aims to provide the application of camptothecin and derivatives thereof as antifouling agent.

The structural formula of the camptothecin or derivatives thereof is as below:

wherein, $R_1$ and $R_2$ are each independently selected from a group consisting of H, amino, cyano, halogen, aldehyde, carboxyl, silyl, $C_1$~$C_8$ alkyl, $C_1$~$C_8$ alkylacyl, $C_1$~$C_8$ alkoxy and di($C_1$~$C_8$ alkyl) amino;

$R_3$ and $R_4$ are each independently selected from a group consisting of H, amino, cyano, halogen, aldehyde, carboxyl, silyl, $C_1$~$C_8$ alkyl, $C_1$~$C_8$ alkylacyl, $C_1$~$C_8$ alkoxy and di($C_1$~$C_8$ alkyl) amino; or wherein $R_3$ and $R_4$ may alternatively form —OCH$_2$O— or —OCH$_2$CH$_2$O— together;

the $C_1$~$C_8$ alkyl is unsubstituted or substituted by a group selected from a group consisting of halogen, cyano, nitro, hydroxyl, $C_1$~$C_8$ alkoxy, $C_1$~$C_8$ alkylamino, di($C_1$~$C_8$ alkyl) amino and tri($C_1$~$C_8$ alkyl) silyl.

The camptothecin and derivatives thereof can be selected from the compounds listed in Table 1. These compounds have already been published (refer to "Li, Y et al., Progress in research of structure modification and structure-activity of camptothecin and its analogues, *Chemical Research and Application*, 2003, 15(6), 744-748"), and all of them can be prepared by known methods in the art.

oxide, zinc pyrithione), isothiazolinone compound (such as 4,5-dichloro-2-n-octyl-4-isothiazolin-3-one), triazine compound (such as N-cyclopropyl-N'-(1,1-dimethylethyl)-6-(methylthio)-1,3,5-triazine-2,4-diamine), N-2,4,6-trichlorophenyl maleimide, pyridinetriphenyl borane, 2-(p-chlorophenyl)-3-cyano-4-bromo-5-trifluoromethyl-pyrrole and N-(fluorodichloro methylthio)-phthalimide.

The present invention also provides an antifouling method for an artificial facility in water, comprising the steps of: antifouling agent of camptothecin or at least one camptothecin derivatives being added into a paint, then the paint mixture being applied to an artificial facility in water; or directly coated on the surfaces of the artificial facility in water; or added into the components of the artificial facility in water; or

TABLE 1

| NO. | Compound Name | $R_1$ | $R_2$ | $R_3$ | $R_4$ |
|---|---|---|---|---|---|
| 1 | Camptothecin (CPT) | H | H | H | H |
| 2 | 10-hydroxyl-CPT | H | H | —OH | H |
| 3 | 10-chloro-CPT | H | H | —Cl | H |
| 4 | 10-bromo-CPT | H | H | —Br | H |
| 5 | 10-cyano-CPT | H | H | —CN | H |
| 6 | 10-nitro-CPT | H | H | —NO$_2$ | H |
| 7 | 10-carboxyl-CPT | H | H | —COOH | H |
| 8 | 10-amino-CPT | H | H | —NH$_2$ | H |
| 9 | 10-methyl-CPT | H | H | —CH$_3$ | H |
| 10 | 10-aminomethyl-CPT | H | H | —CH$_2$NH$_2$ | H |
| 11 | 7-methyl-CPT | —CH$_3$ | H | H | H |
| 12 | 7-ethyl-CPT | —CH$_2$CH$_3$ | H | H | H |
| 13 | 7-hydroxymethyl-CPT | —CH$_2$OH | H | H | H |
| 14 | 7-(2-hydroxyl)ethyl-CPT | —CH$_2$CH$_2$OH | H | H | H |
| 15 | 7-chloromethyl-CPT | —CH$_2$Cl | H | H | H |
| 16 | 7-(2-(methylamino)ethyl)-CPT | —CH$_2$CH$_2$NHCH$_3$ | H | H | H |
| 17 | 7-aldehyde-CPT | —CHO | H | H | H |
| 18 | 7-(2-(trimethylsilyl)ethyl)-CPT | —CH$_2$CH$_2$Si(CH$_3$)$_3$ | H | H | H |
| 19 | 7-ethyl-10-hydroxyl-CPT | —CH$_2$CH$_3$ | H | H | H |
| 20 | 9-methyl-CPT | H | —CH$_3$ | H | H |
| 21 | 9-hydroxyl-CPT | H | —OH | H | H |
| 22 | 9-nitro-CPT | H | —NO$_2$ | H | H |
| 23 | 9-amino-CPT | H | —NH$_2$ | H | H |
| 24 | 9-acetylamino-CPT | H | —NHCOCH$_3$ | H | H |
| 25 | 9-dimethylaminomethyl-10-hydroxyl-CPT | H | —CH$_2$N(CH$_3$)$_2$ | OH | H |
| 26 | 9-aminoethyl-10-hydroxyl-CPT | H | —CH$_2$CH$_2$NH$_2$ | OH | H |
| 27 | 10,11-methylenedioxy-CPT | H | H | —OCH$_2$O— | |
| 28 | 10,11-ethylenedioxy-CPT | H | H | —OCH$_2$CH$_2$O— | |
| 29 | 7-chloromethyl-10,11-methylenedioxy-CPT | —CH$_2$Cl | H | —OCH$_2$O— | |
| 30 | 7-chloromethyl-10,11-ethylenedioxy-CPT | —CH$_2$Cl | H | —OCH$_2$CH$_2$O— | |
| 31 | 9-amino-10,11-methylenedioxy-CPT | H | —NH$_2$ | —OCH$_2$O— | |

The present invention provides application of camptothecin or derivatives thereof as antifouling agent for a facility in water, wherein the antifouling agent contains camptothecin and/or at least one of the derivatives of camptothecin.

Wherein, the facility in water is selected from a group consisting of ships, docks, mariculture netting and cages, offshore oil and gas platforms, buoys, wharves, piers, pipelines, stakes and submerged instruments and equipment.

The present invention provides application of camptothecin or derivatives thereof as antifouling agent for a facility in water. The camptothecin or derivatives thereof can be used to prevent the attachment of marine or freshwater micro-fouling organisms and/or large fouling organisms to the surfaces of a facility in the sea, lake, river or pool.

These inventive antifouling agents can also be used in mixture with other antifouling substance, wherein the other antifouling substance is selected from a group consisting of coppery compound (such as cuprous oxide, copper thiocyanate, copper pyrithione), zincous compound (such as zinc directly dissolved and released into the surrounding water environment of the artificial facility in water.

Wherein, the camptothecin or derivatives thereof has the same meanings as defined before.

The present invention further provides an antifouling paint for artificial facilities in water, which contains:

(1) camptothecin or at least one of the camptothecin derivatives;

(2) at least one binding agent;

(3) at least one solvent.

Wherein, the camptothecin or derivatives thereof has the same meanings as defined before, and the content by weight of the camptothecin or derivatives thereof in the paint is in an amount of 0.1%~60%, preferred 10%~30%.

Wherein, the binding agent (also referred to as film-forming material or binder) may be at least one selected from a group consisting of acrylic resin, perchlorovinyl resin, natural resin (such as rosin), phenolic resin, pitch, alkyd resin, amino resin, chlorinated rubber, vinyl resin, polyester resin, epoxy resin, polyurethane, organic silicon resin and organic fluorine resin; and the solvent may be at least one selected from a group consisting of toluene, xylene, methanol, ethanol, propanol, isopropanol, n-butanol, isobutanol, benzyl alcohol, acetone, butanone, methyl isobutyl ketone, methyl isoamyl ketone, cyclohexanone, 200 # coal tar solvent, butyl acetate and butyl cellosolve.

On the other hand, the antifouling paint for the facilities in water in the present invention may further contain dye and at least one of the following additives: thixotropic agent, dispersing agent, defoaming agent, leveling agent. The dye may be at least one selected from a group consisting of zinc oxide, iron oxide red, talc powder, barium sulfate, calcium carbonate, diatomite, zinc powder and titanium dioxide; and the thixotropic agent may be at least one selected from a group consisting of bentonite, hydrogenated castor oil, polyvinyl alcohol, fumed silica, metal soap; and the dispersing agent may be at least one selected from a group consisting of bentonite, metal soap, hydrogenated castor oil, polyethylene oxide, low-viscosity methyl silicone oil; and the defoaming agent may be selected from a group consisting of tributyl phosphate, polydimethylsiloxane and polyether modified silicone; and the leveling agent may be at least one selected from a group consisting of polyacrylate, modified polyacrylate, multi-fluorinated polyene and polyvinyl butyral.

The antifouling paint may further contain other antifouling substance. The other antifouling substance is selected from a group consisting of coppery compound (such as cuprous oxide, copper thiocyanate, copper pyrithione), zincous compound (such as zinc oxide, zinc pyrithione), isothiazolinone compound (such as 4,5-dichloro-2-n-octyl-4-isothiazolin-3-one), triazine compound (such as N-cyclopropyl-N'-(1,1-dimethylethyl)-6-(methylthio)-1,3,5-triazine-2,4-diamine), N-2,4,6-trichlorophenyl maleimide, pyridinetriphenyl borane, 2-(p-chlorophenyl)-3-cyano-4-bromo-5-trifluoromethyl-pyrrole, N-(fluorodichloro methylthio)-phthalimide.

Common preparation methods for paints can be used to prepare the antifouling paint. The antifouling paint of the present invention may be applied to the artificial facilities in water by conventional means like dipping, spraying or coating.

Experiments show that camptothecin and derivatives thereof have significant inhibitory activity for the attachment of fouling organisms, i.e. antifouling activity, thus they can be used to prevent the attachment of fouling organisms to the surfaces of artificial facilities in water. The extraction process of camptothecin is mature and various derivatives can be obtained through structural modifications of camptothecin, moreover, many preparation methods for derivatives of camptothecin have been publicly reported.

Experiments show that camptothecin and derivatives thereof have high antifouling activity, good antifouling efficiency and a broad spectrum of antifouling. According to the biological model tests in laboratory, the camptothecin and derivatives thereof in the present invention have shown significant inhibitory effect on attachment of the fouling organisms in water, and have antifouling activity to both of the marine micro-fouling organisms and the marine large fouling organisms. On the other hand, the marine antifouling paints prepared with the compounds stated in the present invention as antifouling agents by conventional methods have shown good antifouling effects through panel tests in natural sea area, and the antifouling term is more than one year. The paints have effectively prevented the attachment of various marine fouling organisms like barnacles, mussels, oysters, sea squirts, sponges and bryozoans, and have shown a broad-spectrum antifouling effect, which has verified the test results in laboratory. Besides, the use of the antifouling agents of the present invention in the artificial facilities in water like mariculture netting and buoyant rafts also has shown high efficient, broad-spectrum antifouling effect, and has gained good antifouling application effect, which has further definitized the application potential of camptothecin and derivatives thereof as novel antifouling agents.

How to prevent the marine artificial facilities from marine biofouling without polluting the marine environment is currently a major problem in human's development and utilization of marine resources. The advantages of using the antifouling agent prepared with camptothecin and derivatives thereof are: no toxic heavy metal compound, no environmental pollution but being helpful to protect the marine ecological environment, good antifouling effect, and wide application prospect.

DETAILED DESCRIPTION OF THE PREFERRED EMBODIMENTS

Example 1

Tests for Inhibitory Effects of CPT and Derivatives Thereof on the Attachment of Fouling Organisms (1) Test for Inhibitory Effect on the Attachment of Barnacles Barnacles are sessile Cirripedia with calcareous shells and widespread. They firmly attach to the surfaces of vessels and various offshore artificial facilities, and are one of the major marine fouling organisms as well as one of the major target organisms in the study of antifouling technology. Adults of *Balanus albicostatus* were collected from the rocks and piers at Baicheng Coast in Xiamen, and their cypris larvas were obtained by culturing in laboratory. It is the attachment of the cypris larvas that causes the barnacles to change from swimming life to attaching life. Thus, inhibition of the attachment of the cypris larvas can verify the antifouling activity of the compounds. CPT and 10-hydroxyl-CPT were dissolved in ethyl acetate respectively, and a series of concentration gradient were set according to the results of pre-experiment. 1 ml of each solution was taken to a petri dish respectively, 1 ml of ethyl acetate was taken to another blank petri dish serving as control group. After the solvents evaporated completely and the compounds were distributed evenly on the bottom surfaces and the side surfaces of the petri dishes, each petri dish was added with 10 ml of membrane filtrated seawater (filtrated by membrane with pore size of 0.22 μm, the same below). Each experimental group and control group had 3 paralleled cups, and each cup was added with about 30 cypris larvas of *Balanus albicostatus*. Stereomicroscope was used to observe the attachment of the cypris larvas 48 h after the addition, and the $EC_{50}$ values of CPT and 10-hydroxyl-CPT, which are half inhibition concentrations for the attachment of cypris larvas of *Balanus albicostatus*, were determined. ($EC_{50}$ refers to the effective concentration for inhibiting 50% of the attachment of the tested organisms. The lower the value is, the higher the antifouling activity will be, the same below.)

Figure 1:
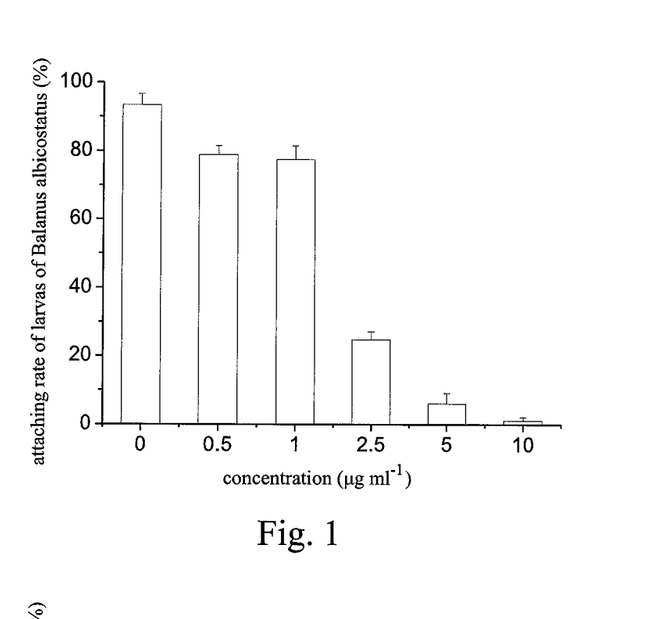
FIG. 1 shows the inhibitory effect of CPT on the attachment of cypris larva of *Balanus albicostatus*.
Figure 2:
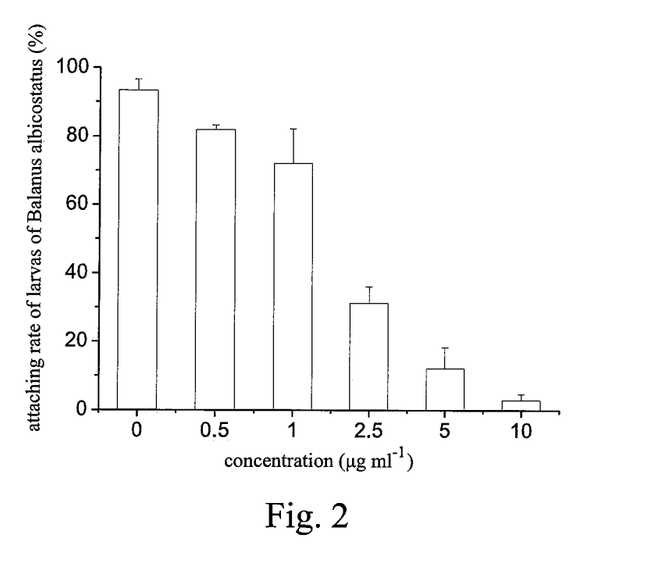
FIG. 2 shows the inhibitory effect of 10-hydroxyl-CPT on the attachment of cypris larva of *Balanus albicostatus*.

The test results are showed in FIGS. 1 and 2. The results show that CPT and 10-hydroxyl-CPT can both significantly inhibit the attachment of cypris larvas of *Balanus albicostatus* at low concentration, showing efficient antifouling activity. The half inhibition concentrations ($EC_{50}$) of CPT and 10-hydroxyl-CPT for the attachment were 1.73 μg $ml^{-1}$ and 1.78 μg $ml^{-1}$ respectively.

(2) Test for Inhibitory Effect on the Attachment of *Bugula*

Bugulas are marine bryozoan and widespread in various sea areas in the world. They often attach to the surfaces of marine artificial facilities like mariculture netting, cages, vessels, buoys, etc., and they are important marine fouling organisms as well. *Bugula neritina*, also called multicellular *Bugula*, its adults were collected from the fish culture net bins in Western sea area of Xiamen and put into an aquarium filled with fresh seawater after back to the laboratory to induce the release of their swimming larvas. It is the attachment of their swimming larvas that causes the Bugulas to change from swimming life to attaching life. Thus, inhibition of the attachment of the swimming larvas can verify the antifouling activity of the compounds. CPT and 10-hydroxyl-CPT were dissolved in ethyl acetate respectively, and a series of concentration gradient were set according to the results of pre-experiment. 1 ml of each solution was taken to a petri dish respectively; 1 ml of ethyl acetate was taken to another blank petri dish serving as control group. After the solvents evaporated completely and the compounds were distributed evenly on the bottom surfaces and the side surfaces of the petri dishes, each petri dish was added with 10 ml of membrane filtrated seawater. Each experimental group and control group had 3 paralleled cups, and each cup was added with about 30 larvas of *Bugula neritina*. Stereomicroscope was used to observe the attachment of the larvas of *Bugula neritina* 48 h after the addition, and the half inhibition concentrations for the attachment of larvas of *Bugula neritina*, $EC_{50}$ values of CPT and 10-hydroxyl-CPT were determined.

Figure 3:
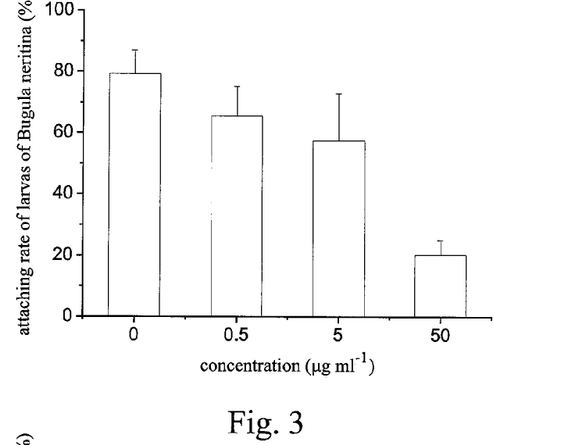
FIG. 3 shows the inhibitory effect of CPT on the attachment of larva of *Bugula neritina*.
Figure 4:
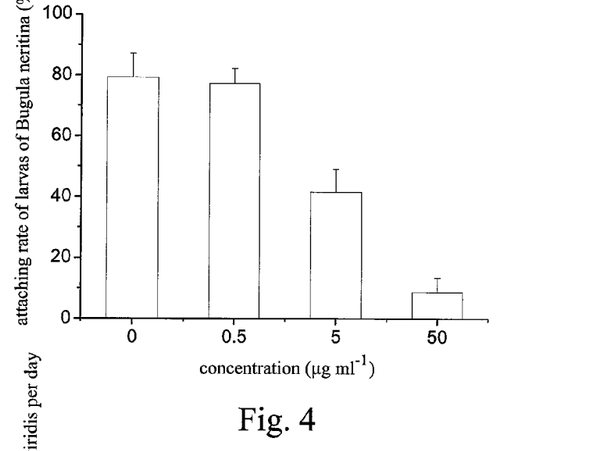
FIG. 4 shows the inhibitory effect of 10-hydroxyl-CPT on the attachment of larva of *Bugula neritina*.

The test results are showed in FIGS. 3 and 4. The results show that CPT and 10-hydroxyl-CPT have significant inhibitory effect on the attachment of larvas of *Bugula neritina*, and the $EC_{50}$ values were 15.02 μg $ml^{-1}$ and 5.93 μg $ml^{-1}$ respectively.

(3) Test for Inhibitory Effect on the Attachment of Mussels by Produced Byssal Threads Mussels are common bivalve in marine fouling biocenoses, widespread, and are one of the major target organisms in the study of marine antifouling technology. Mussels explore surfaces by their feet, looking for attachment substrate. If proper surfaces for attaching were found, mussels would produce byssal threads to attach to them. Thus if the compounds inhibited mussels to produce byssal threads, the compounds could be proved to have antifouling activity. *Perna viridis* were collected from the fish net bins in offshore sea area of Zhangzhou, and in which those with shell length of 1.4~2.4 cm were selected and washed with seawater, followed by gent cut-off of the byssal threads. And then the *Perna viridis* were washed with membrane filtrated seawater. CPT were first dissolved in a trace of dimethyl sulfoxide, and then mixed with membrane filtrated seawater to prepare a series of concentration gradient. 4 ml of each solution was taken into a 12-well plate, and each well was added with one *Perna viridis*. 4 ml of membrane filtrated seawater containing a trace of dimethyl sulfoxide and one *Perna viridis* were added into the control group. Each experimental group and control group had 8 paralleled groups. After 24-hours culture at room temperature, the amount of byssal threads produced by *Perna viridis* were observed, and the half inhibition concentration of CPT for the attachment of *Perna viridis* by produced byssal threads, $EC_{50}$, were determined.

Figure 5:
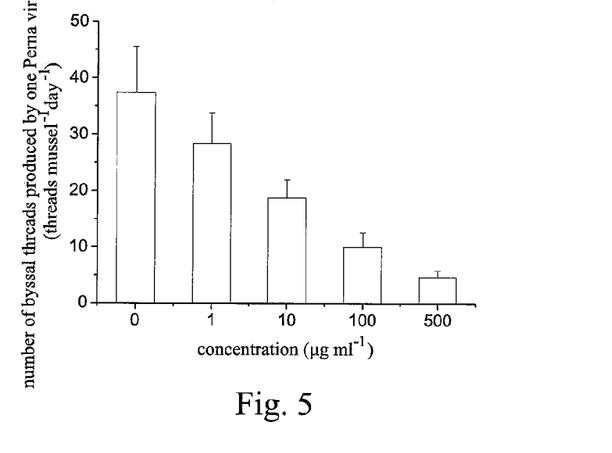
FIG. 5 shows the inhibitory effect of CPT on the production of byssal threads of *Perna viridis*.

The test results are showed in FIG. 5. The results show that CPT has significant inhibitory effect on the attachment of *Perna viridis* by produced byssal threads, the $EC_{50}$ value was 10.78 μg $ml^{-1}$.

The other representative CPT derivatives listed in Table 1 were tested by the same above methods, and generally the values of $EC_{50}$ were lower than 200 μg $ml^{-1}$, which also had significant inhibitory effect on the attachment of fouling organisms, showing antifouling activity.

Example 2

Preparation of Antifouling Paint Containing CPT

CPT was well mixed with acrylic resin, rosin, iron oxide red, thixotropic agent and organic solvent, and also glass beads were added. The mixture was stirred in high-speed dispersion machine until the fineness of the paints was around 80 μm, then the glass beads were removed by filtration with 100-mesh tulle, followed by discharge and obtaining the antifouling paint.

Example 3

Preparation of Antifouling Paints Containing Compound of CPT and Other Antifouling Agent Marine antifouling paints containing compound of CPT and another antifouling agent were prepared by the same method stated in Example 2. The types and weight ratios for the compound of CPT and another antifouling agent respectively were CPT:$Cu_2O$ (4:1), CPT:$Cu_2O$ (2:1), CPT:$Cu_2O$ (1:1), CPT:TCPM (1:1), CPT:ZnPt (1:1). Five different marine antifouling paints were prepared according to the types and weight ratios above, wherein TCPM is N-2,4,6-trichlorophenyl maleimide, ZnPt is Zinc pyrithione.

Example 4

Antifouling Efficiency in Sea Area Test for Antifouling Paint Containing CPT and Paints Containing Compound of CPT and Another Antifouling Agent As shown in Table 2, the tested antifouling agents were provided in three large groups: 1) CPT; 2) compound of CPT and another antifouling agent; 3) existing common antifouling agent (as positive control). All of the tested antifouling agents had a weight ratio of 20% to the marine antifouling paints.

TABLE 2

Results of panel test in sea area

| antifouling agents in the paints | coverage ratio of fouling organisms (%, Mean ± SE) | | | |
|---|---|---|---|---|
| | after 3 months | after 6 months | after 9 months | after 12 months |
| 1) CPT | 0.15 ± 0.12 | 11.6 ± 6.68 | 9.03 ± 2.64 | 39.67 ± 10.43 |
| 2) compound of CPT and another antifouling agent | | | | |
| CPT:Cu$_2$O (4:1) | 0 | 5.87 ± 4.75 | 18.06 ± 7.87 | 61.05 ± 13.07 |
| CPT:Cu$_2$O (2:1) | 0.84 ± 0.68 | 28.56 ± 14.79 | 62.77 ± 11.68 | 67.63 ± 13.07 |
| CPT:Cu$_2$O (1:1) | 1.65 ± 0.90 | 54.24 ± 16.94 | 70.16 ± 16.43 | 90.85 ± 4.96 |
| CPT:TCPM (1:1) | 0.85 ± 0.14 | 30.12 ± 5.37 | 61.32 ± 23.09 | 86.93 ± 8.47 |
| CPT:ZnPt (1:1) | 0.44 ± 0.16 | 10.01 ± 4.32 | 35.10 ± 2.71 | 94.07 ± 3.71 |
| 3) existing common antifouling agent | | | | |
| Cu$_2$O | 7.23 ± 2.02 | 91.75 ± 2.90 | 70.91 ± 13.40 | 98.88 ± 0.48 |
| CuPt | 13.09 ± 2.71 | 37.20 ± 11.69 | 43.11 ± 15.25 | 94.69 ± 1.01 |
| paint with none antifouling agent | 82.88 ± 7.48 | 90.16 ± 4.15 | 72.13 ± 10.16 | 95.41 ± 1.49 |

Note:
TCPM is N-2,4,6-trichlorophenyl maleimide, ZnPt is Zinc pyrithione, CuPt is Copper pyrithione.

The panel test in natural sea area was carried out referring to the national standard GB/T5370-2007 "Method for testing antifouling panels in shallow submergence". The prepared antifouling paints each were evenly coated on the epoxy resin panels; paints with none antifouling agent and prepared by the same methods were provided as negative control; each coated sample had 6 paralleled groups. The tested panels were fixed in iron frames after the paints had dried, and they were hanged on the test buoyant rafts in the sea area near Dalipu Island in Xiamen in June, 2010. After the tested panels had been immersed in seawater up to 3, 6, 9 and 12 months, they were then photographed, and the coverage ratios of the fouling organisms in each coated sample areas were analyzed and counted. Herein, the coverage ratio of the fouling organisms is the ratio of surface area covered by marine large fouling organisms in the sample area divided by the whole surface area in the sample area (the same below), and the lower the value is, the higher the antifouling efficiency will be.

The results of antifouling efficiency in sea area test on the prepared antifouling paints are shown in Table 2. During the test, the major large fouling organisms attaching to the tested panels were barnacles, mussels, oysters, sea squirts, sponges and bryozoans, etc. As can be seen from Table 2, the coverage ratios of the coated sample area with prepared antifouling agents containing CPT were far lower than the coverage ratios of the control coated sample area with none antifouling agent, which indicates that the paints prepared with CPT as antifouling agent have efficient antifouling performance, and the antifouling term is up to 12 months. As also can be seen from Table 2, among the antifouling agents which were used in the preparation of the paints with the same content of 20% (by weight), CPT had better antifouling efficiency in sea area than the existing common antifouling agents of cuprous oxide (Cu$_2$O) and copper pyrithione (CuPt). On the other hand, the compounds of CPT and another antifouling agent of Cu$_2$O, TCPM or ZnPt also showed certain antifouling efficiency, in which the CPT:Cu$_2$O (4:1) had the best antifouling efficiency. However, both the antifouling efficiencies and the antifouling terms of the group of compounds were not as good as the group of pure CPT, which further verifies that CPT has efficient antifouling activity.

Example 5

Test for the Application of Antifouling Paint Containing CPT on the Mariculture Netting (an Artificial Facility in Water)

The preparation method of antifouling paint containing CPT was the same as stated in Example 2, the weight ratio of CPT in the antifouling paint was also set to 20%. Dip coating method was used, and the nettings were immersed in each of the prepared paints respectively, and then taken out to dry in the air. The nettings were fixed on plastic frames by ribbons respectively and hanged in the mariculture area of nacre in Lingshui of Hainan in November, 2010. Paint with none antifouling agent and prepared by the same method was provided as negative control; the antifouling paint for wooden boats (chlorinated rubber as base material and cuprous oxide as major antifouling agent) which was bought from market was provided as positive control; the clean netting that had never immersed in any paint was provided as blank control. Each tested group had 3 paralleled groups. After the tested nettings had been immersed in seawater up to 3, 6, 9 and 12 months, they were then photographed, and the coverage ratios of the fouling organisms on the nettings respectively were analyzed and counted.

The results of the test for application on the mariculture netting are shown in Table 3. During the test, the major large fouling organisms attaching to the nettings were bugulas, hydroides, sponges, sea squirts, oysters and seaweeds, etc. As can be seen from Table 3, the coverage ratios of fouling organisms on the nettings that coated with antifouling paint containing CPT were far lower than the nettings coated with none paint, which indicates that the antifouling paint containing CPT has good antifouling effect on mariculture netting, and the antifouling term is up to 12 months. On the other hand, the paint group with none antifouling agent did not show any antifouling effect, which indicates that the outstanding antifouling efficiency of marine antifouling paint containing CPT was derived from the antifouling activity of CPT. Besides, it also can be seen from Table 3 that the antifouling efficiency of marine antifouling paint containing CPT on the netting was better than the antifouling paint containing Cu$_2$O as main antifouling agent. Generally, the results of the test indicate that the marine antifouling paint containing CPT has good antifouling application effect on mariculture netting.

TABLE 3

The results of the test for application on mariculture netting

| tested groups | coverage ratio of fouling organisms (%, Mean ± SE) | | | |
| --- | --- | --- | --- | --- |
| | after 3 months | after 6 months | after 9 months | after 12 months |
| marine antifouling paint group with CPT | 2.45 ± 0.42 | 2.19 ± 0.60 | 3.89 ± 1.07 | 9.64 ± 2.66 |
| antifouling paint with $Cu_2O$ as main antifouling agent | 5.23 ± 1.78 | 79.61 ± 4.27 | 64.60 ± 11.62 | 95.98 ± 2.55 |
| paint with none antifouling agent | 85.00 ± 6.30 | 99.82 ± 0.05 | 69.08 ± 8.00 | 99.52 ± 0.24 |
| blank control with no paint | 71.16 ± 10.13 | 99.92 ± 0.03 | 54.83 ± 5.24 | 99.70 ± 0.21 |

Example 6

Test for Application of Antifouling Paint Containing CPT on the Floating Bed (an Artificial Facility in Water)

The preparation method of marine antifouling paint containing CPT was the same as stated in Example 2, the weight ratio of CPT in the marine antifouling paint was also set to 20%. The prepared paint was evenly coated on each floating bed component in the same specification (the floating bed component was a plastic foam board of 30×30 cm, coated with a plastic woven bag). After the paints had dried, the floating bed components were fixed on bamboo frames, and hanged in the Yundang Lake in Xiamen (previously a natural harbor, due to the construction of the dam, it has become substantially enclosed artificial lagoon and exchanges part of water with western sea area of Xiamen each day) in August, 2010. Paint with none antifouling agent and prepared by the same method was provided as negative control; the antifouling paint for wooden boats (chlorinated rubber as base material and cuprous oxide as major antifouling agent) which was bought from market was provided as positive control; clean floating bed components that had never coated with any paint were provided as blank control. Each tested group had 3 paralleled groups. After the tested floating bed components had been immersed in seawater up to 3, 6, 9 and 12 months, they were then photographed, and the coverage ratios of the fouling organisms on the floating bed component were analyzed and counted.

The results of test for application on the floating bed are shown in Table 4. During the test, the major large fouling organisms attachting to the floating bed components were barnacles, bugulas, oysters, *Mytilopsis salleis*, sea squirts, and seaweeds, etc. As can be seen from Table 4, the coverage ratios of fouling organisms on the floating bed components that coated with antifouling paint containing CPT were far lower than the floating bed components coated with none paint, which indicates that the antifouling paint containing CPT has good antifouling effect on floating bed components, and the antifouling term is up to 12 months. On the other hand, the paint group with none antifouling agent did not show any antifouling effect, which indicates that the outstanding antifouling efficiency of marine antifouling paint containing CPT was derived from the antifouling activity of CPT. Besides, it also can be seen from Table 4 that the antifouling efficiency of marine antifouling paint containing CPT on the floating bed components was better than the antifouling paint containing $Cu_2O$ as main antifouling agent. Generally, the results of the test indicate that the marine antifouling paint containing CPT also has good antifouling application effect on floating bed.

TABLE 4

The results of the test for application on floating bed

| tested groups | coverage ratio of fouling organisms (%, Mean ± SE) | | | |
| --- | --- | --- | --- | --- |
| | after 3 months | after 6 months | after 9 months | after 12 months |
| marine antifouling paint group with CPT | 0.02 ± 0.01 | 0 | 29.32 ± 5.85 | 50.85 ± 15.11 |
| antifouling paint with $Cu_2O$ as main antifouling agent | 0.20 ± 0.10 | 31.78 ± 11.38 | 49.26 ± 8.32 | 98.27 ± 1.73 |
| paint with none antifouling agent | 0.63 ± 0.29 | 50.87 ± 1.16 | 38.69 ± 3.64 | 99.97 ± 0.03 |
| blank control group with no paint | — | 52.82 ± 5.56 | 50.89 ± 2.16 | 100 ± 0 |

Note:

"—" means the photos of the group in that month were forgotten to taken, and the coverage ratio of fouling organisms of this group was not counted.

The invention claimed is:

1. A method of antifouling, comprising administration of a compound having the structural formula:

wherein, $R_1$ and $R_2$ are each independently selected from a group consisting of H, amino, cyano, halogen, aldehyde, carboxyl, silyl, $C_1$-$C_8$ alkyl, $C_1$-$C_8$ alkylacyl, $C_1$-$C_8$ alkoxy and di($C_1$-$C_8$ alkyl) amino;

$R_3$ and $R_4$ are each independently selected from a group consisting of H, amino, cyano, halogen, aldehyde, carboxyl, silyl, $C_1$-$C_8$ alkyl, $C_1$-$C_8$ alkylacyl, $C_1$-$C_8$ alkoxy and di ($C_1$-$C_8$ alkyl) amino; or $R_3$ and $R_4$ form —OCH$_2$O— or —OCH$_2$CH$_2$O— together;

the compound being administered to a facility in water selected from the group consisting of ships, docks, mariculture netting, cages, offshore oil and gas platforms, buoys, wharves, piers, pipelines, stakes and submerged instruments and equipment, and combinations thereof.

2. The method according to claim 1, wherein the $C_1$-$C_8$ alkyl is unsubstituted or substituted by a group selected from a group consisting of halogen, cyano, nitro, hydroxyl, $C_1$-$C_8$ alkoxy, $C_1$-$C_8$ alkylamino, di ($C_1$-$C_8$ alkyl)amino and tri ($C_1$-$C_8$ alkyl) silyl.

3. The method according to claim 1, wherein the compound is selected from the listed compounds:

| NO. | Compound Name | $R_1$ | $R_2$ | $R_3$ | $R_4$ |
|---|---|---|---|---|---|
| 1 | Camptothecin (CPT) | H | H | H | H |
| 2 | 10-hydroxyl-CPT | H | H | —OH | H |
| 3 | 10-chloro-CPT | H | H | —Cl | H |
| 4 | 10-bromo-CPT | H | H | —Br | H |
| 5 | 10-cyano-CPT | H | H | —CN | H |
| 6 | 10-nitro-CPT | H | H | —NO$_2$ | H |
| 7 | 10-carboxyl-CPT | H | H | —COOH | H |
| 8 | 10-amino-CPT | H | H | —NH$_2$ | H |
| 9 | 10-methyl-CPT | H | H | —CH$_3$ | H |
| 10 | 10-aminomethyl-CPT | H | H | —CH$_2$NH$_2$ | H |
| 11 | 7-methyl-CPT | —CH$_3$ | H | H | H |
| 12 | 7-ethyl-CPT | —CH$_2$CH$_3$ | H | H | H |
| 13 | 7-hydroxymethyl-CPT | —CH$_2$OH | H | H | H |
| 14 | 7-(2-hydroxyl)ethyl-CPT | —CH$_2$CH$_2$OH | H | H | H |
| 15 | 7-chloromethyl-CPT | —CH$_2$Cl | H | H | H |
| 16 | 7-(2-(methylamino)ethyl)-CPT | —CH$_2$CH$_2$NHCH$_3$ | H | H | H |
| 17 | 7-aldehyde-CPT | —CHO | H | H | H |
| 18 | 7-(2-(trimethylsilyl)ethyl)-CPT | —CH$_2$CH$_2$Si(CH$_3$)$_3$ | H | H | H |
| 19 | 7-ethyl-10-hydroxyl-CPT | —CH$_2$CH$_3$ | H | H | H |
| 20 | 9-methyl-CPT | H | —CH$_3$ | H | H |
| 21 | 9-hydroxyl-CPT | H | —OH | H | H |
| 22 | 9-nitro-CPT | H | —NO$_2$ | H | H |
| 23 | 9-amino-CPT | H | —NH$_2$ | H | H |
| 24 | 9-acetylamino-CPT | H | —NHCOCH$_3$ | H | H |
| 25 | 9-dimethylaminomethyl-10-hydroxyl-CPT | H | —CH$_2$N(CH$_3$)$_2$ | OH | H |
| 26 | 9-aminoethyl-10-hydroxyl-CPT | H | —CH$_2$CH$_2$NH$_2$ | OH | H |
| 27 | 10,11-methylenedioxy-CPT | H | H | —OCH$_2$O— | |
| 28 | 10,11-ethylenedioxy-CPT | H | H | —OCH$_2$CH$_2$O— | |
| 29 | 7-chloromethyl-10,11-methylenedioxy-CPT | —CH$_2$Cl | H | —OCH$_2$O— | |
| 30 | 7-chloromethyl-10,11-ethylenedioxy-CPT | —CH$_2$Cl | H | —OCH$_2$CH$_2$O— | |
| 31 | 9-amino-10,11-methylenedioxy-CPT | H | —NH$_2$ | —OCH$_2$O—. | |

4. The method according to claim 1, wherein the antifouling agent is used to prevent the attachment of marine or freshwater large fouling organisms to the surfaces of the facility in the sea, lake, river or pool.

5. The method according to claim 1, wherein the antifouling agent is used in mixture with other antifouling substance, wherein the other antifouling substance is one member selected from a group consisting of coppery compound, zincous compound, isothiazolinone compound, triazine compound, N-2,4,6-trichlorophenyl maleimide, pyridinetriphenyl borane, 2-(p-chlorophenyl)-3-cyano-4-bromo-5-trifluoromethyl-pyrrole and N-(fluorodichloro methylthio)-phthalimide;
wherein the coppery compound is one member selected from a group consisting of cuprous oxide, copper thiocyanate and copper pyrithione; and the zincous compound is one member selected from a group consisting of zinc oxide and zinc pyrithione; and the isothiazolinone compound is 4,5-dichloro-2-n-octyl-4-isothiazolin-3-tone; and the triazine compound is N-cyclopropyl-N'-(1,1-dimethylethyl)-6-(methylthio)-1,3,5-triazine-2,4-diamine.

6. The method according to claim 1, comprising the steps of:

the compound of the structural formula:

being added into a paint, then the paint mixture being applied to the facility in water; or
directly coated on the surfaces of the facility in water; or
added into the components of the facility in water; or
directly dissolved and released into the surrounding water environment of the facility in water.

* * * * *